United States Patent [19]

Singleton et al.

[11] Patent Number: 5,462,660
[45] Date of Patent: Oct. 31, 1995

[54] HIGH PERFORMANCE LIQUID CHROMATOGRAPHY INJECTION SYSTEM FOR THE SIMULTANEOUS CONCENTRATION AND ANALYSIS OF TRACE COMPONENTS

[75] Inventors: John A. Singleton, Apex; Larry F. Stikeleather, Raleigh, both of N.C.

[73] Assignee: The United States of America as represented by the Secretary of Agriculture, Washington, D.C.

[21] Appl. No.: 243,951

[22] Filed: Apr. 22, 1994

[51] Int. Cl.⁶ ................................................ B01D 15/08
[52] U.S. Cl. ........................ 210/198.2; 210/659; 422/70
[58] Field of Search ........................... 210/635, 656, 210/659, 198.2; 96/104, 105; 422/70

[56] References Cited

U.S. PATENT DOCUMENTS

| | | | |
|---|---|---|---|
| 3,458,437 | 7/1969 | Ouano | 210/198.2 |
| 3,630,371 | 12/1971 | Hrdina | 210/198.2 |
| 3,686,117 | 8/1972 | Lauer | 210/198.2 |
| 4,070,284 | 1/1978 | Fujita et al. | 210/31 |
| 4,112,743 | 9/1978 | Mowery, Jr. | 73/61.1 C |
| 4,154,583 | 5/1979 | Favre | 210/198.2 |
| 4,158,630 | 6/1979 | Stearns | 210/198.2 |
| 4,274,967 | 6/1981 | Snyder | 210/198.2 |
| 4,314,823 | 2/1982 | Rich | 210/198.2 |
| 4,446,105 | 5/1984 | Dinsmore | 210/198.2 |
| 4,454,043 | 6/1984 | Ting | 210/198.2 |
| 4,500,432 | 2/1985 | Poole | 210/198.2 |
| 4,544,485 | 10/1985 | Pinkerton | 210/198.2 |
| 4,554,071 | 11/1985 | Ruijten et al. | 210/198 |
| 4,577,492 | 3/1986 | Holba | 210/198.2 |
| 4,597,943 | 7/1986 | Sugiyama | 210/198.2 |
| 4,699,718 | 10/1987 | Jones | 210/198.2 |
| 4,724,081 | 2/1988 | Kawahara | 210/198.2 |
| 4,835,707 | 5/1989 | Amano et al. | 364/497 |
| 4,942,018 | 7/1990 | Munk | 422/70 |
| 4,950,397 | 8/1990 | Oguendo | 210/198.2 |
| 4,952,126 | 8/1990 | Hanaoka | 210/198.2 |
| 4,992,168 | 2/1991 | Takayama | 210/198.2 |
| 5,071,547 | 12/1991 | Cazer | 210/198.2 |
| 5,093,267 | 3/1992 | Miura | 210/198.2 |
| 5,100,787 | 3/1992 | Shimizu et al. | 435/131 |
| 5,104,622 | 4/1992 | Binder | 210/198.2 |
| 5,117,109 | 5/1992 | Asakawa | 210/198.2 |
| 5,135,718 | 8/1992 | Kawaguchi | 210/198.2 |
| 5,183,750 | 2/1993 | Nishide et al. | 435/134 |
| 5,234,599 | 8/1993 | Cortes | 210/198.2 |
| 5,236,593 | 8/1993 | Cortes | 210/198.2 |

OTHER PUBLICATIONS

Martinez et al., "Sensitive Method for the Determination of Organophosphorus Pesticides in Fruits and Surface waters by High–Performance Liquid chromatography with Ultraviolet Detection" Journal of Chromatograpy 607:37–45. 1992.

Spalik et al., "Rapid Two–Step Preconcentration Procedure for Aldicarb Determination in Water by High–Performance Liquid Chromatography Using a 254–nm Detector" Journal of Chromatography 253:289–294. 1982.

Drexler et al., Proceedings American Peanut Research and Education Soc. 11:57. 1979.

Primary Examiner—Ernest G. Therkorn
Attorney, Agent, or Firm—M. Howard Silverstien; John Fado; Gail E. Poulos

[57] ABSTRACT

A high pressure liquid chromatography injection system with two independently controlled valves and a pump is provided which permits the simultaneous and independent concentration and analysis of trace components using two different solvent systems.

6 Claims, 5 Drawing Sheets

5,462,660

HIGH PERFORMANCE LIQUID CHROMATOGRAPHY INJECTION SYSTEM FOR THE SIMULTANEOUS CONCENTRATION AND ANALYSIS OF TRACE COMPONENTS

FIELD OF THE INVENTION

The present invention relates to a novel high performance liquid chromatography (HPLC) injection system. It further relates to a method for simultaneous concentration and separation of substances using the novel system.

DESCRIPTION OF THE ART

High performance liquid chromatography (HPLC) is generally used for identification and determination of the concentration of substances dissolved or dispersed in liquids. It is also used to separate substances on a preparative scale. When substances are present in trace amounts, a preconcentration step is necessary prior to analysis on HPLC. Preconcentration steps, such as, for example, extractions and/or column clean-up, are time consuming and usually require large volumes of solvents. Therefore, there is a need for a system which allows direct injection of a sample into an HPLC apparatus which permits simultaneous concentration and analysis of substances. This type of system would be useful for analyzing substances of environmental concern such as, for example, pesticides and herbicides in water, soil, or on agricultural commodities; or for detecting the presence of explosives in water. Furthermore, it would be useful for on-line cleanup and/or concentration of pharmaceutical samples. Also, a system of this type would be useful in food quality and quality control. For example, concentration of phospholipids or 1-2 and 1-3 diglycerides from seed oils to detect oil adulteration and heat abuse in oils and processed food products, on-line cleanup of sugar extracts from food products, concentration of soft drink additives, elimination of carbohydrates for quantitative analysis of organic acids in fruit juices and wine, concentration and/or monitoring neutral fermentation products to isolate products or determine health of fermentation cultures, determination of nitrates and nitrites in meats, and determination of monosodium glutamate in meats.

There are various prior art apparatus for concentrating and analyzing trace components. U.S. Pat. No. 4,835,707 describes a system that includes an automatic filtration, concentration, and injection apparatus, which is separate from an HPLC, where a filtrate of a reaction product is adsorbed onto a concentration column with water and is then continuously guided into an HPLC system. This system uses two six-way valves for introducing sample from the concentration column to the analytic column of an HPLC, a water pump for introducing a sample to a concentration column and an analytic pump for feeding the sample from the concentration column into an HPLC. One six-way valve connects the filtration device through a sampling loop to another six-way valve which connects the sampling loop to the concentration column and then provides a pathway to elute the sample from the concentration column to the HPLC.

U.S. Pat. No. 4,554,071 describes a chromatography system for separating and/or detecting substances that are present in trace amounts which includes a concentration column and an analytic column. The concentration column is preloaded with sample, connected to the analytic column via a coupling member and a gradient elution is used to move the substance off the concentration column onto the separation column, and off the separation column where fractions are collected.

U.S. Pat. No. 4,070,284 discloses a liquid chromatography apparatus for concentrating and separating non-ionic trace components in large sample volumes. One embodiment includes a concentration column, a separation column, three three-way valves, and two pumps (FIG. 1). A pump 4 feeds the sample from sample solution tank 1 onto a concentration column 6. Pump 4 then feeds the sample from concentration column 6 onto separation column 7 by pumping desorbing solution from desorbing solution tank 2 through concentration column 6. Another disclosed embodiment for analyzing ionic trace components (FIG. 4) has a pump 32 for loading the sample onto a concentration column 29 and a separate pump 26 which elutes the sample off concentration column 29. Pump 32 also feeds washing solution from tank 35 onto concentration column 29 prior to sample loading. Two switch valves, 33 and 27 are required to wash the concentration column and load the sample. Sample-loaded concentration column 29 is again washed by pumping washing solution from tank 35 with pump 32. Next, the six-way valve is switched so that pump 26 pumps eluting fluid from tank 36 onto the concentration column and onto the separation column. At this point, the samples are separated and detected while separation takes place, the concentration column is washed, new sample loaded and washed.

U.S. Pat. No. 4,112,743 describes a high pressure liquid chromatography system that employs two multi-port valve means 6, 16 two pumps 10, 14 (one high pressure and one low pressure), and a single column 2 for analysis of a sample. High pressure pump 10 is used to pass a first carrier liquid through the system and to propel a second carrier liquid from carrier chamber 26 into the rest of the apparatus. The second carrier liquid is pumped into chamber 26 with low pressure pump 14.

While various apparatus have been developed for separating and analyzing trace components by high pressure liquid chromatography, there still remains a need in the art for a more effective system for economically analyzing trace components. The present invention provides a cost-effective, alternative strategy which is different from prior art apparatus.

SUMMARY OF THE INVENTION

It is, therefore, an object of the present invention to provide a high pressure liquid chromatography injection system which includes flow path means for analyzing trace components in a sample while independently and simultaneously equilibrating a concentration column.

A further object of the present invention is to provide a high pressure liquid chromatography injection system which has at least two independently controlled multi-port valves and a first pumping means.

A still further object of the present invention is to provide a high pressure liquid chromatography injection system which has a concentration column and an analysis and/or semiprep column which are equilibrated independently and simultaneously using two different solvent systems.

Another object of the present invention is to provide a high pressure liquid chromatography injection system which allows the concentration column to be loaded with a new sample while the previous sample is analyzed.

A further object of the present invention is to provide a method for simultaneously concentrating and analyzing trace components in a sample using a high pressure liquid chromatography injection system which has at least two independently controlled multi-port valves and a first pumping means.

DETAILED DESCRIPTION OF THE INVENTION

The analysis of phospholipids in peanut oil is used as a model system. The apparatus and method are applicable to the analysis and/or separation of any trace components dissolved or dispensed in liquids. The apparatus is described with reference to disclosed figures in which the same numbers are used.

Figure 1:
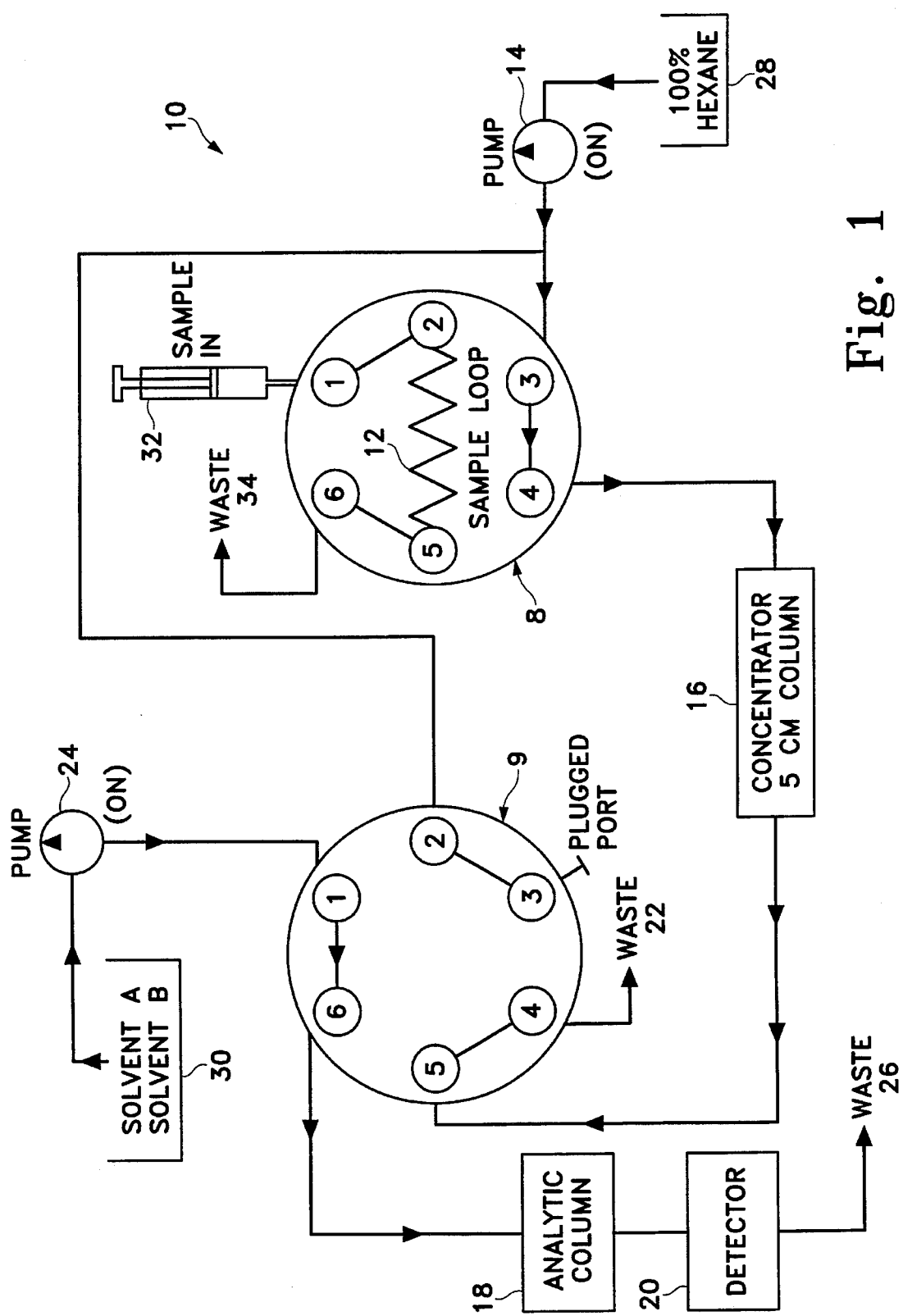
FIG. 1 shows a schematic view of the injection system with the valve positions and solvent flow path in the equilibration stage.

Referring to FIG. 1, which is the equilibration stage, high pressure liquid chomatography (HPLC) injection system (IS) 10 includes two six port valves 8, 9 mounted on an HPLC interconnected with an injection or sample loop 12, a high pressure isocratic single piston pump 14, referred to as first pumping means, a Humphrey switch (not shown), a concentration or guard column 16, and a semiprep or analysis column 18. Pump 14 is connected to port 3 on valve 8. The concentration column 16 is connected to port 4 on valve 8 and to port 5 on valve 9. The concentration column is 50 mm×4 mm. The column packing material is selected based on the components which will be analyzed. A C18 reverse phase column, for example, would be used to concentrate such chemicals as trace organocholine pesticides in water, phenoxy acid herbicides, polyaromatic hydrocarbons, pathalate esters, phenols, explosives in water, soft drink additives, neutral fermentation products, nitrates and nitrates in meats, monosodium glutamate in meats, citrates in pharmaceutical samples, and parabens from pharmaceuticals. Phospholipids from seeds can be, for example, concentrated on a silica column. 1-2 and 1-3 diglycerides can be, for example, concentrated on a cyano column. The concentration column can be a cation column for clean up of sugar extracts from food products. It also can be an anion exchange column for the analysis of organic acids in fruit juices and wine, for example.

Port 5 in valve 9 is connected with port 4 which is connected to waste container 22. Analysis or semiprep column 18 is connected to port 6 of valve 9. Analysis or semiprep column 18 is 100 mm×8 mm column. The packing material for the analysis or semiprep column is the same as that used for concentration column 16 as described above.

Column 18 is also connected to detector 20. Although not limited thereto, detector 20 is preferably a high sensitivity detector such as an ultraviolet light detector capable of accurately determining the concentration of the trace components. Samples from the analysis or semiprep column can then be collected using a collector means or eluted to waste flask 22. In the above described configuration, both columns 16 and 18 can be equilibrated independently and simultaneously using two different solvent systems. Two flow path means for the equilibration stage are depicted in FIG. 1. The first means, an equilibration flow path means, includes solvent container 28 with fluid flowing to pump 14, ports 3 and 4 in valve 8, to concentration column 16, ports 5 and 4 of valve 9 and out to waste container 22. The second flow path means, the injection flow path means, includes solvent container 30, pump 24, herein referred to as a second pumping means, ports 1 and 6 of valve 9, analysis column 18, detector 20 and waste container 26.

Figure 2:
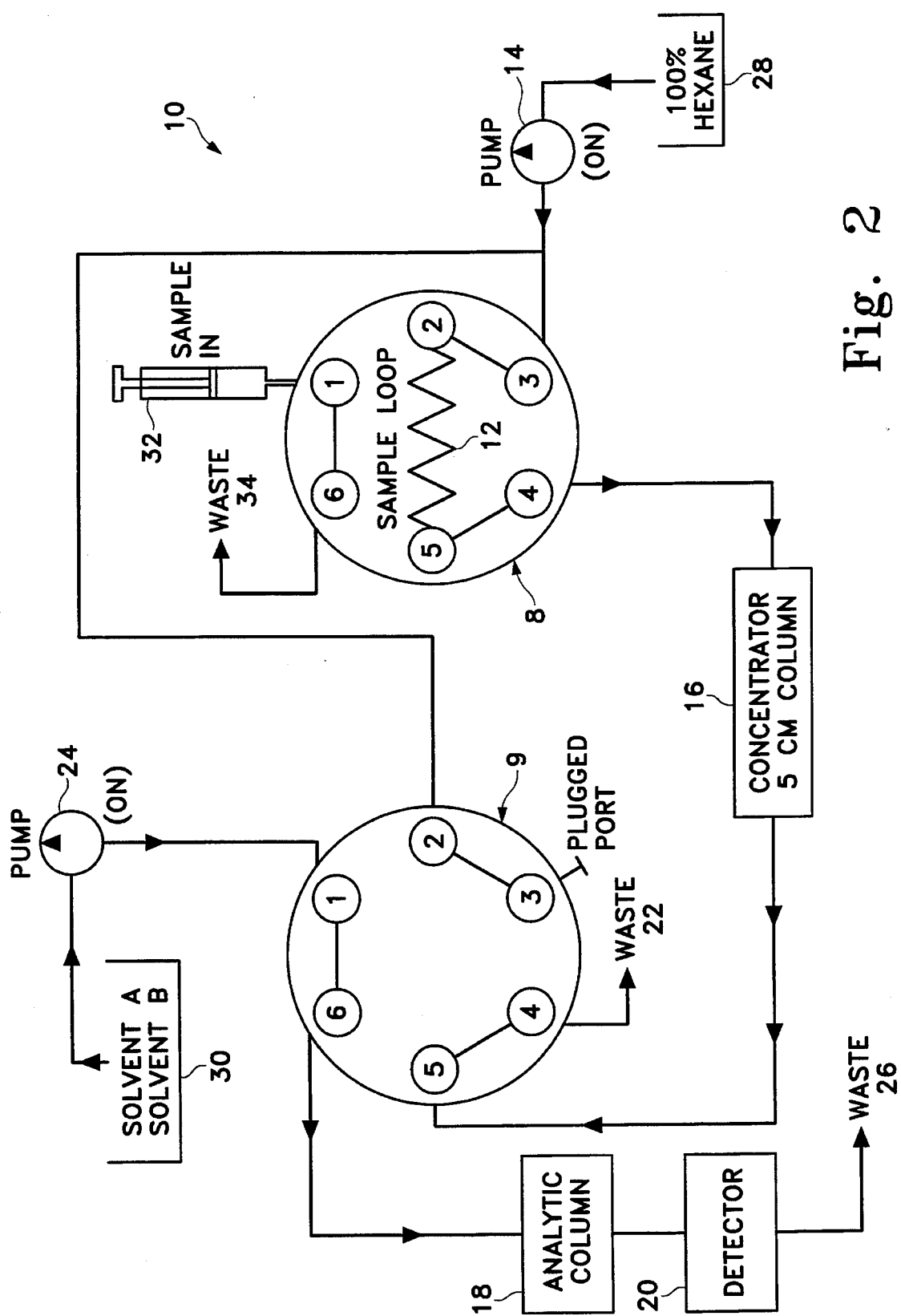
FIG. 2 shows a schematic view of the injection system with the valve positions and solvent flow path in the load stage.

In FIG. 2, the load stage, valve 8 is switched by a control output from a microprocessor which outputs an electrical signal (110 v) to a pneumatic solenoid valve (not shown) to activate valve 8 located in the HPLC to inject the sample in sample loop 12 onto concentration column 16. The flow path means for the load stage are depicted in FIG. 2. The first flow path means during the load stage includes solvent container 28, pump 14, port 3 in valve 8, sample loop 12, ports 5 and 4 in valve 8, concentrating column 16, ports 5 and 4 in valve 9, and waste container 22. The second flow path means during load stage is the same as described above for the second flow path means for the equilibration stage.

Figure 3:
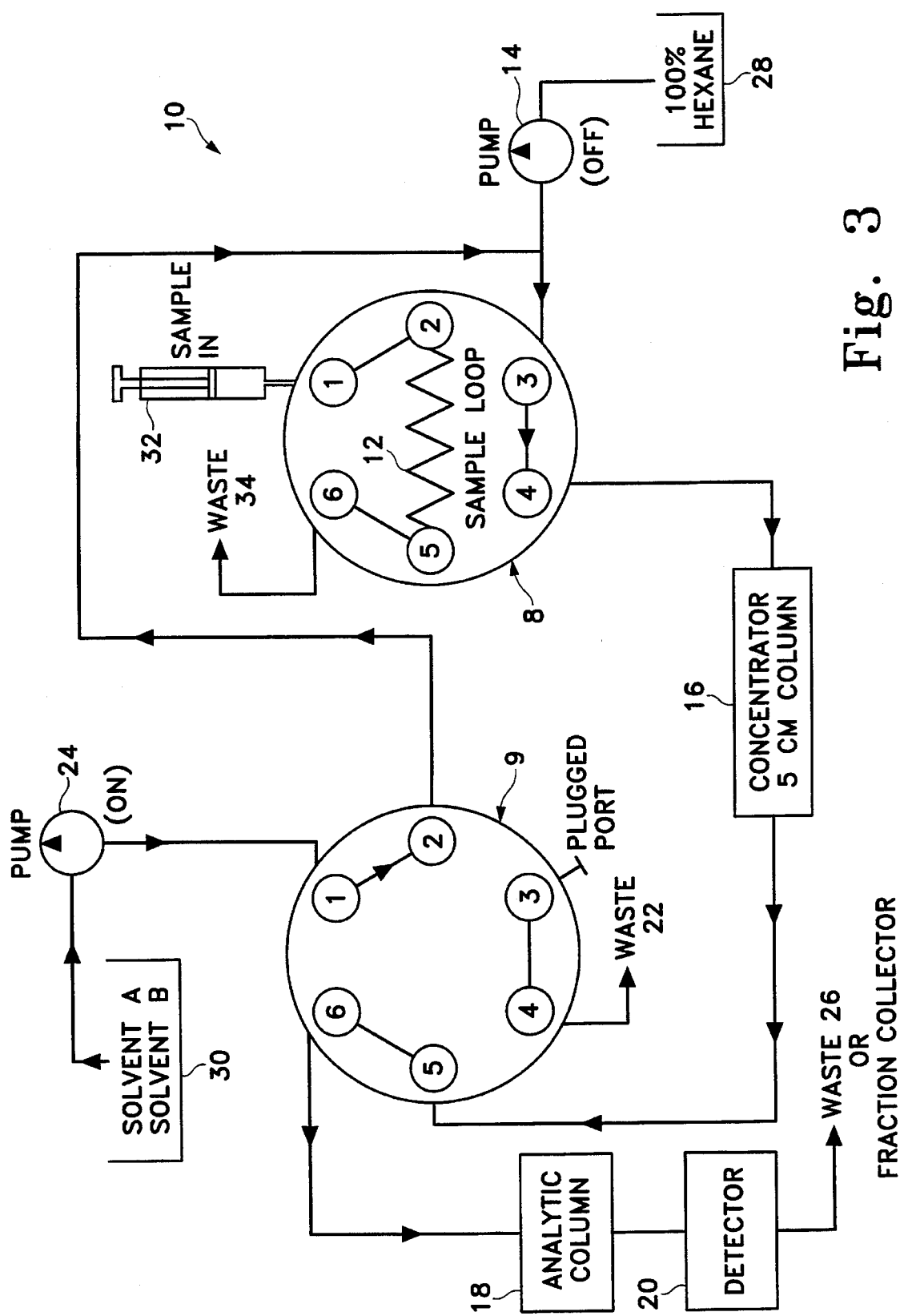
FIG. 3 shows a schematic view of the injection system with the valve positions and solvent path in the analysis stage.
Figure 4B:
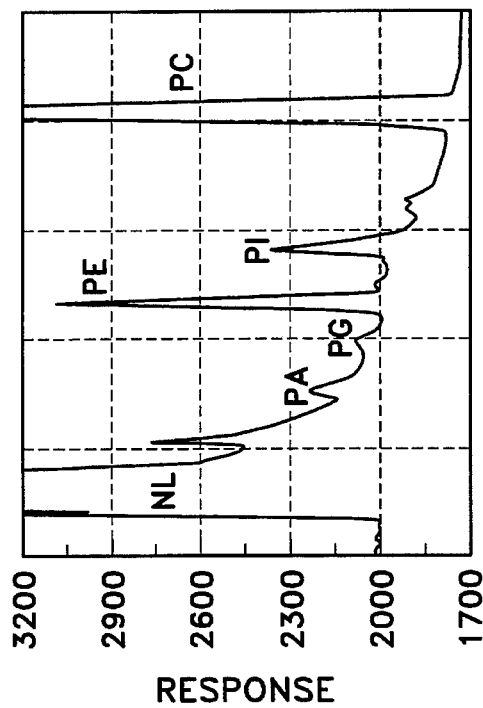
FIG. 4 shows an HPLC chromatogram of the effects of different postharvest treatments (A) undamaged, (B) immature, (C) high temperature cured, (D) freeze damaged, on the phospholipid profile of peanuts.
Figure 4D:
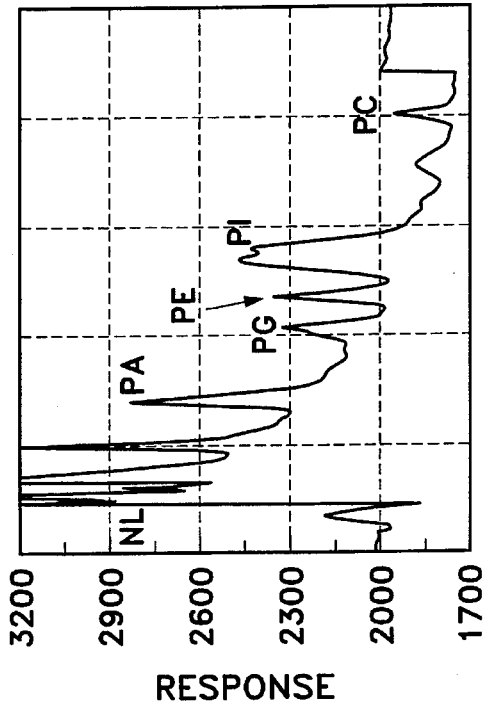
Figure 4A:
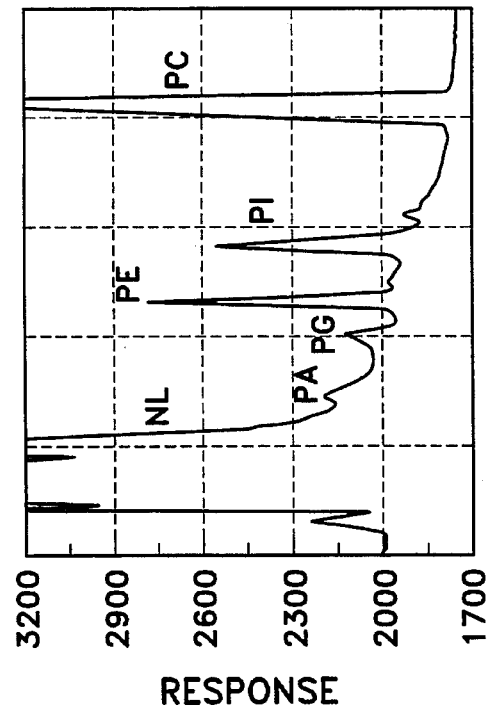
Figure 4C:
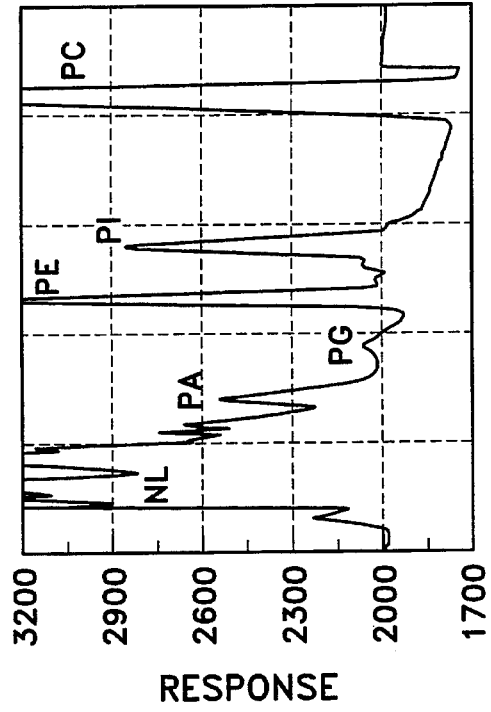

In FIG. 3, the analysis stage, pump 14 is turned off temporarily, the Humphrey air switch is manually thrown which activates valve 9 sending an eluate from pump 24 through concentration column 16 eluting the sample onto analysis column 18 where the sample is separated. The Humphrey switch is a two-way manual pneumatic switch (not shown) which supplies air pressure to activate valve 9. This can also be done electronically and can be controlled by the computer or by the integrator via the time events program. Once the sample is off column 16, valves 8 and 9 are switched back to the configuration shown in FIG. 2, the load stage. The concentration column can then be reloaded for the next analysis while the previous sample is being analyzed. The flow path means for the analysis stage are depicted in FIG. 3. The first flow path means includes solvent container 30, pump 24, ports 1 and 2 of valve 9, ports 3 and 4 of valve 8, concentration column 16, ports 5 and 6 of valve 9, analysis column 18, detector 20, and waste or fraction collector 26. After the sample is off column 16 and onto column 18, valves 8 and 9 are switched back to load stage configuration to repeat the process.

In operation, pump 14 and pump 24 are turned on allowing columns 16 and 18 to be equilibrated simultaneously using two different solvent systems. During this equilibration stage (FIG. 1) sample is injected into sample loop 12 via ports 1 and 2 of valve 8 using sample injector 32.

After the sample is injected into loop 12, valve 8 is switched by control output from the microprocessor and sample in loop 12 is injected onto concentration column 16. This is called the load stage (see FIG. 2). The desired components are retained on concentration column 16 while the remaining components of the sample are eluted to waste container 22 via valve 9, ports 5 and 4.

Next, pump 14 is turned off, Humphrey air switch (not shown) is manually turned on which activates valve 9 sending solvent from solvent container 30 through pump 24 into concentration column 16 eluting the retained components onto column 18 (see FIG. 3). After all the sample has been eluted from concentration column 16 (approximately 2 minutes), valves 8 and 9 are both switched by air pressure back to the load position (FIG. 2). Valve 9 is switched using the manual Humphrey switch and valve 8 is switched by the microprocessor in the HPLC as described above. A new sample is injected into sample loop 12 and the process is repeated. The sample on column 18 is analyzed by eluting fractions through detector 20. The fractions can either be collected with fraction collector 26 or eluted to waste container 26 after flowing through detector 20.

The following examples illustrate the use of this injection system for concentration and analysis of phospholipids in peanut oil. The examples are intended to further illustrate the invention and are not intended to limit the scope as defined by the claims.

Preharvest and postharvest conditions affect the quality of crude peanut oil and the overall quality of peanuts for edible purposes. Heavy rains during the harvest season, exposure to freezing temperatures, immature harvest, and drying at a higher temperature than those recommended are major factors contributing to a low quality raw product. These stress events result in the activation of enzymes such as lipases and lipoxygenase resulting in the breakdown of lipid constituents, production of hydroperoxides, and increased volatile production.

The phospholipid concentration of peanuts is low, approximately 1%. However, it is a very important lipid fraction due to some of its unique properties. Phospholipids are the major constituents of cell membranes, are highly polar and have a high degree of unsaturation. When peanuts are damaged, cells become leaky. Organic constituents such as enzymes, amino acids, carbohydrates, metals, and cations are leached out of the cells. The metabolic activity of the cells changes drastically resulting in production of off-flavors in the raw product. In many cases this renders the product unusable for edible purposes and complicates the refining of the crude oil. The disclosed HPLC injection system allows the simultaneous concentration and analysis of the low concentration of peanut phospholipids.

EXAMPLE 1

Peanuts (VA NC7) were grown at the North Carolina State Experiment Station, Lewiston, N.C. (NC) using accepted cultural practices and were treated to four different post harvest conditions. A control sample, post harvest condition one, was dried to approximately 25% moisture in a windrow and finally mechanically dried to 6% moisture using ambient temperature. Immature peanuts, post harvest condition two, were hand harvested in early August and the percentage of immature kernels was determined to be 40% by the hull scrape method (Drexler et al., Proceedings American Peanut Research and Education Soc. 11:57, 1979, herein incorporated by reference). The immature sample was dried to 6% moisture using ambient temperature. A sample, harvested like the above described control sample, was freeze damaged by placing the peanuts in shallow metal pans in a freezer at $-20°$ C. (set temperature of freezer) for 8 hours. This is post harvest condition three. The internal peanut temperature was monitored by placing a thermocouple into the center of a seed and logging the temperature with an Easy Logger Recording System (Omnidata Internation, Logan, Utah). The final peanut internal temperature was $-16°$ C. After freezing, the peanuts were thawed and mechanically dried to 6% moisture using ambient temperature. The fourth post harvest condition was a high temperature sample cured at $40°$ C. and mechanically dried to 6% moisture using ambient temperature. All samples were stored in the shell at $45°$ C. and 60% relative humidity until analyzed. Peanuts were not sized prior to treatment.

EXAMPLE 2

Lipids were extracted from the four sets of peanuts using chloroform/methanol ($CHCl_3$/MEOH) in a volume ratio of approximately about 2:1. All solvents used in the extraction were of reagent grade. A 50 gram sample was blended with 300 ml of $CHCl_3$/MEOH (2:1) in a Sorvall blender (Ivan Sorvall Inc., Norwalk, Colo.) for one minute. The slurry was filtered through a double thickness filter paper using a buchner funnel and a water aspirator. A saturated solution of NaCl was added to the filtered solution in a separatory funnel, shaken, and allowed to stand until phase separation occurred. The $CHCl_3$ layer was saved and the water layer was discarded. The solvent layer was washed two more times with saturated NaCl and the $CHCl_3$ was removed by flash evaporation. Extracted lipid material was stored in a freezer at $-20°$ C. until analyzed.

EXAMPLE 3

Peanut phospholipids were concentrated on a silica concentration column that is 50 mm×4 mm and contains 40 micron particle size silica. Concentration column 16 is equilibrated with 100% hexane which is HPLC grade (Fisher Scientific, Pittsburgh, Pa.). As seen in FIG. 1, pump 14 pumps hexane through column 16, to port 4 of valve 9, to port 5 of valve 9, and into waste container 22. Pump 24 pumps a solvent solution of 2-propanol/hexane in a volume:volume ratio of approximately about 4:3 (4/3) through analysis column 18 by pumping the eluate through ports 1 and 6 of valve 9. The solvent flows through column 18, detector 20 into waste container 26. Both columns are equilibrated independently and simultaneously using two different solvents as described above. During this stage, 1 ml of peanut oil is injected into sample loop 12 in valve 8 using sample injector 32.

Next valve 8 is switched by control output from a microprocessor so that sample loop 12 is connected to ports 2 and 5 of valve 8. This starts the load stage as depicted in FIG. 2. Valve 9 retains the same configuration of the equilibration stage. 100% hexane is pumped by pump 14 through the sample loop 12 via port 3 and 2 in order to inject the oil in loop 12 onto concentration column 16. The phospholipids are adsorbed onto column 16 and the bulk triglyceride fraction is eluted to waste container 22. Once the sample has been adsorbed onto concentrator column 16, pump 14 is turned off and Humphrey air switch (not shown) is manually thrown activating valve 9 which sends the 2-propanol/hexane (4/3) from pump 24 through column 16 eluting the adsorbed phospholipids onto analysis column 18 where they are separated. When the phospholipids have been eluted from concentration column 16 (approximately 2 minutes) both valves are switched again placing the configuration back in the load position (FIG. 2) and pump 14 is turned back on. Concentration column 16 can be reloaded with a new sample for the next analysis while the previous sample is being analyzed.

The first sample of peanut phospholipids is separated on analysis column 18 which is a 100 mm×8 mm column containing 40 micron particle size silica using a gradient program of mixed solvents as described in Table 1 below and a flow rate of 1.5 ml/minute. Solvent A is isopropanol/hexane in a volume/volume ratio of approximately about 4:3.0. Solvent B is isopropanol/hexane/water in a volume/volume/volume ratio of approximately about 3:6:1.5. Phospholipids are identified by retention times by running authentic phospholipid standards (Sigma Chemical Company, St. Louis, Mo.) under the same conditions. The major phospholipids of peanut oil are phosphatidic acid (PA), phosphatidylglycerol (PG), phosphatidylethanolamine (PE), phosphalidylinositol (PI), and phosphatidylcholine (PC). These standards were concentrated and separated using the above described conditions. Individual phospholipids were collected manually and stored at −20° C. for further analysis. Triplicate analyses were run on each sample for comparative purposes and multiple analyses were run for collection of individual phospholipids.

TABLE 1

HPLC Gradient Program for Peanut Phospholipid Separation

| Time | % A | % B |
|---|---|---|
| 0 | 100 | 0 |
| 20.0 | 0 | 100 |
| 35.0 | 0 | 100 |
| 35.1 | 100 | 0 |
| 45.0 | 100 | 0 |

FIG. 4 shows typical HPLC chromatograms for the above described four different postharvest treatments. Individual phospholipids were identified by retention time of known standards and have been previously characterized by mass spectrometry (not shown). Some unidentified components are probably hydroperoxides of phospholipids which are present in freeze damaged samples.

Table 2 shows the concentration of the five individual phospholipids and how they are affected by postharvest stress. All comparisons are made relative to the control.

TABLE 2

Effect of Postharvest Stress on Phospholipid Composition[1]

| Sample | Phospholid Composition[2] | | | | | Total PL[3] |
|---|---|---|---|---|---|---|
| | PA | PG | PE | PI | PC | |
| Control | 2.18 | 2.47 | 13.3 | 15.7 | 66.4 | 1 |
| Immature | 2.37 | 1.3 | 14.1 | 7.88 | 74.4 | 1.33 |
| HT Cured | 10.8 | 1.31 | 7.89 | 18.1 | 68.5 | 1.5 |
| Freeze Damaged | 12.4 | 6.15 | 18.4 | 3.83 | 3.87 | 1.07 |

[1]Average of three reps
[2]Relative percent by HPLC
[3]Control set to 1

In immature peanuts, there is a slight increase in the concentration of PA and PE whereas PG and PI decreased when compared to the control. PC increased about 8% above the control. This may be explained on the basis that in immature oil seeds PA and PC are the precursors to the other phospholipids. Total phospholipids in the immature sample is 1.33 times the concentration of the control.

When peanuts are subjected to heat stress, cells become leaky and the metabolic changes activate lipase enzymes and lipoxygenase. In the heat damaged sample, PA and PI increased and a slight increase was observed in PC concentration (Table 2). PE decreased which may be due to oxidation since it is the most unsaturated of the peanut phospholipids. Increases in the other phospholipids was probably due to an increase in unsaturation. Some of the increase may have been at the expense of the neutral fraction. The total phospholipids is 1.5 times the control. Heat stress is known to increase unsaturation resulting in increased fluidity of the lipid membranes. However, if heat stress is prolonged or the temperature is excessive, the phospholipid bilayer becomes disoriented and the proteins become immobile leading to the oxidation of unsaturated lipids.

In the freeze damage sample, it can be seen in Table 2 that PA, PG, and PE increased whereas PI and PC decreased. PI contains a reducing sugar and is active in oxidation reduction reactions. PC does not have the same antioxidant properties of some of the other phospholipids and apparently was oxidized heavily as shown in Table 2. The total phospholipid content in the freeze damage sample was 1.07 times the control, reflecting considerable oxidation of the phospholipid as noted by the amount of PC in the sample. It is well established that freeze injury leads to an increase in lipid unsaturation, an increase in the phospholipid fraction, and an increase in free phosphorous. During freeze damage, respiration becomes anaerobic and the phospholipid bilayer becomes more solidified restricting protein movement. At this stage, cellular constituents leach out, changing the metabolic activity of the cells. Unsaturated lipids are highly susceptible to oxidation during this process. Freeze damage of peanuts resulted in the almost complete oxidation of PC.

EXAMPLE 4

Collected phospholipid fractions (Example 3) are further purified by adding hexane and water, in a volume:volume ratio of approximately about 50:50 (50/50), to the collected fraction to create a two phase system for the control, immature, and high temperature cured samples for the analysis of molecular species of PC. The water phase was saved and re-extracted with $CHCl_3$/MEOH (2/1). Each sample was further concentrated by flash evaporation prior to analysis on HPLC as described above. Analysis column 18 for this example is a C18 reverse phase column (Surpleco Inc., Bellefonte, Pa.) with a 3 micron particle size. The samples were eluted using an isocratic elution with MEOH/Acetonitrile/Water in a ratio of approximately about 91%:3%:6% volume:volume:volume. Sample of PC from each treatment for molecular species analysis was 1 ml injected via a 1 ml sample loop. A flow rate of 1.5 ml/min was used and molecular species were detected with a UV detector at 205 nm.

Figure 5:
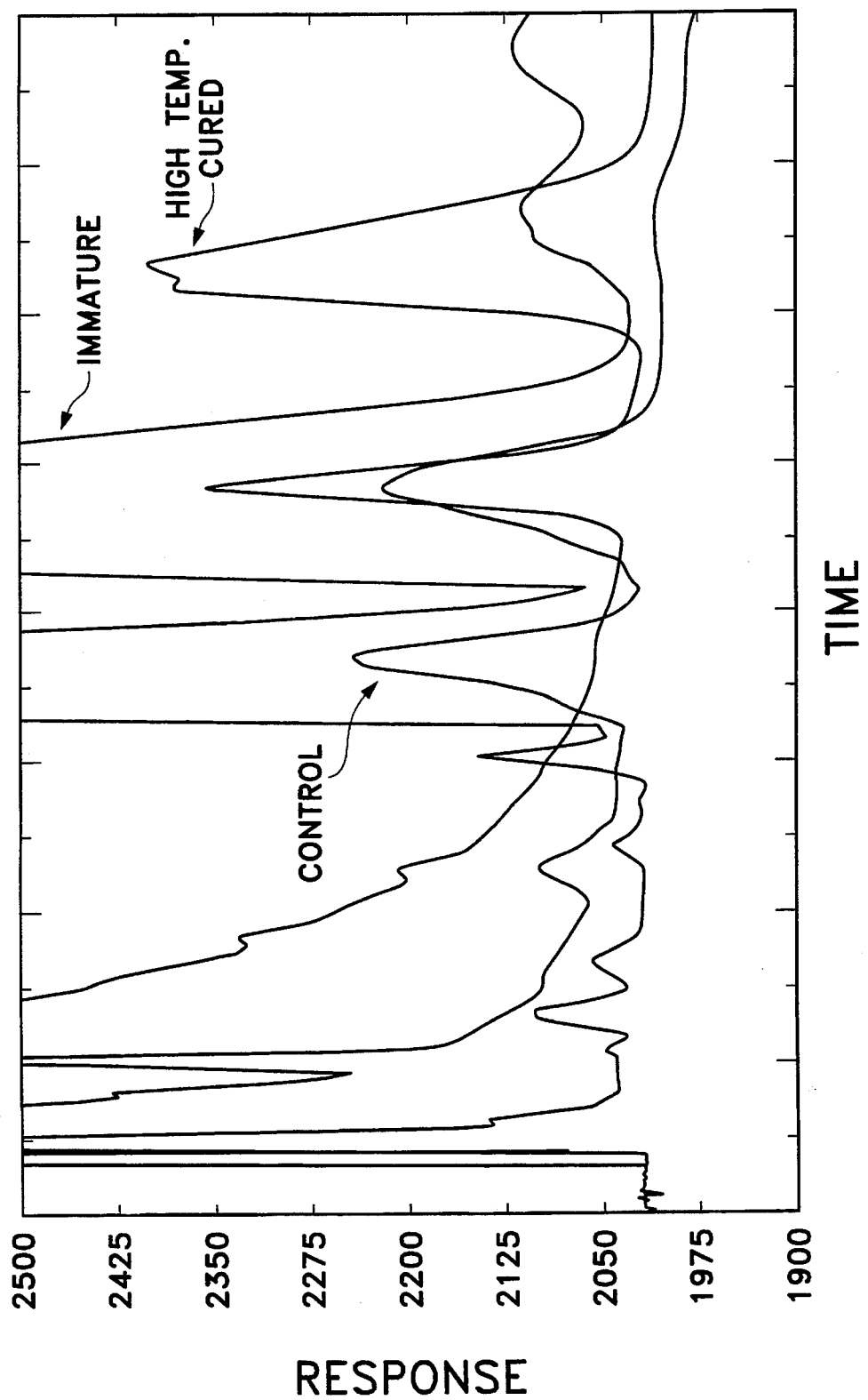
FIG. 5 shows an HPLC chromatogram on the effect of immaturity and high temperature on the molecular species profile of phosphatidylcholine.

FIG. 5 shows the separation of the molecular species of phosphatidyl choline (PC) in the control, immature, and high temperature cured samples. Due to the destruction of PC in the freeze damage sample, the concentration was too low to permit analysis of this fraction. The phospholipid molecular species containing fatty acid moiety's with the most unsaturation will elute first on reverse phase columns followed by the more saturated molecular species. Comparison of the molecular species peaks of PC, from different postharvest treatments, show both qualitative and relative quantitative differences. Sample size injected for each treatment was one mL. Immature peanuts have a much higher concentration of unsaturated molecular species represented by the two large peaks in the sample which are probably the C18:2/C18:2 and the C18:1/C18:2 species. Both of these molecular species have been identified in peanuts by HPLC and mass spectrometry. Molecular species found in the high temperature cured sample reflected a more saturated nature. This was probably due to the oxidation of some of the more unsaturated molecular species by heat stress. Phospholipids act in a synergistic manner with tocopherols lengthing the onset of the induction period of lipid oxidation. The degree of unsaturation of the acyl fatty acid chains has an added effect on the length of the induction period.

This model describes the use of the disclosed HPLC apparatus and method for the simultaneous concentration and analysis of trace components and collection of samples for further analysis. The foregoing detailed description is for the purpose of illustration. Others skilled in the art can apply the knowledge described to other trace components. Such detail is solely for that purpose and those skilled in the art can make variations therein without departing from the spirit and scope of the invention.

INDEX OF ELEMENTS 1 port 2 port 3 port 4 port 5 port 6 port 8 six port valve 9 six port valve 10 HPLC injection system (IS) 12 injection loop 14 high pressure single piston pump, first pumping means 16 concentration or guard column 18 semiprep or analytic column 20 detector 22 waste container 24 high pressure single piston pump, second pumping means 26 waste container or fraction collector 28 solvent container 30 solvent container 32 sample injector 34 waste container

We claim:

1. A high pressure liquid chromatography apparatus comprising an injection system for simultaneously concentrating and analyzing trace components which includes a first multi-port valve that includes a sample loop and an injection port and provides an equilibration flow path means and an injection flow path means for equilibrating a concentration column and injecting sample into the apparatus, a second multi-port valve for providing an equilibration flow path means for equilibrating an analysis column and providing an analysis flow path means for transferring sample on a concentration column to an analysis column and a detector means, an first pumping means for pumping a first solvent for equilibrating said concentration column, and a concentration column, wherein said analysis flow path means for analyzing trace components includes a second pumping means in fluid communication with a second solvent container and at least two ports of said second multi-port such that a solvent from said second solvent container flows through said at least two ports of the second multi-port valve out to at least two ports of the first multi-port valve, a second multi-port valve in fluid communication with said second pumping means and said first multi-port valve and is in fluid communication with said concentration column and said analysis column through at least two ports different from said ports in fluid communication with said second pumping means and the first multi-port valve, a first multi-port valve in fluid communication with said second multi-port valve and said concentration column such that solvent flows from said second multi-port valve through at least two ports of said first multi-port valve to said concentration column, a concentration column in fluid communication with said first multi-port valve and said second multi-port valve such that solvent flows through said concentration column from first multi-port valve to at least two ports in said second multi-port valve and into an analysis column, and an analysis column in fluid communication with at least two ports in the second multi-port valve and a detector such that solvent flows from said second multi-port valve through the analysis column and into said detector.

2. The high pressure liquid chromatography apparatus of claim 1 wherein said equilibration flow path means for equilibrating said concentration column includes said first pumping means in fluid communication with a first solvent container and at least two ports of said first multi-port valve such that a solvent from said first container flows in said valve to said concentration column, said first multi-port valve in fluid communication with said first pumping means and said concentration column, said concentration column in fluid communication with said first multi-port valve and at least two ports of said second multi-port valve such that the concentration column is in fluid communication with a second waste container, and said second multi-port valve which is in fluid communication with said concentration column and said second waste container.

3. The high pressure liquid chromatography apparatus of claim 1 wherein said equilibration flow path means for equilibrating an analysis column includes a second pumping means in fluid communication with a second solvent container and at least two ports of said second multi-port valve such that a solvent from said second solvent container flows in said valve to said analysis column, said second multi-port valve in fluid communication with said second pumping means and said analysis column, and said analysis column in fluid communication with said second multi-port valve and a detector means.

4. The high pressure liquid chromatography apparatus of claim 1 wherein said injection flow path means for injecting sample into said apparatus includes said first pumping means in fluid communication with said first solvent container and said sample loop of the first multi-port valve such that solvent from said first container flows from said pump, through said sample loop by way of at least four ports and into said concentration column, said first multi-port valve wherein the sample loop is in fluid communication with at least four ports such that said first solvent flows from said first pumping means, through said sample loop, by way of at least four ports, to said concentration column, a concentration column in fluid communication with said first multi-port valve and at least two ports of said second multi-port valve such that the concentration column is in fluid communication with a second waste container, and a second multi-port valve which is in fluid communication with said concentration column and said second waste container.

5. The apparatus of claims 1, 2, 3, or 4 wherein said apparatus includes a means for switching the valves in order to form the different flow paths.

6. The apparatus of claim 1 wherein said means for switching the valves is a microprocessor.

* * * * *